(12) United States Patent
Kraemer et al.

(10) Patent No.: US 7,766,847 B2
(45) Date of Patent: Aug. 3, 2010

(54) PUNCTURING DEVICE

(75) Inventors: Uwe Kraemer, Ilvesheim (DE); Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/845,051

(22) Filed: Aug. 25, 2007

(65) Prior Publication Data

US 2008/0064986 A1 Mar. 13, 2008

(30) Foreign Application Priority Data

Aug. 25, 2006 (EP) ................... 06017713

(51) Int. Cl.
*A61B 5/00* (2006.01)
*A61B 17/14* (2006.01)
*A61B 17/32* (2006.01)
*A61B 17/34* (2006.01)
*A65D 81/00* (2006.01)

(52) U.S. Cl. .............. 600/584; 600/583; 606/181; 606/182; 606/183; 606/184; 606/185

(58) Field of Classification Search .......... 600/583–584, 600/573; 606/181–185
See application file for complete search history.

(56) References Cited

U.S. PATENT DOCUMENTS

| | | | | |
|---|---|---|---|---|
| 5,879,311 | A | * | 3/1999 | Duchon et al. .............. 600/583 |
| 5,971,941 | A | * | 10/1999 | Simons et al. .............. 600/573 |
| 6,093,156 | A | | 7/2000 | Cunningham et al. |
| 2003/0143113 | A2 | * | 7/2003 | Yuzhakov et al. ............ 422/56 |
| 2003/0171699 | A1 | | 9/2003 | Brenneman |
| 2003/0199790 | A1 | * | 10/2003 | Boecker et al. .............. 600/576 |
| 2003/0212344 | A1 | | 11/2003 | Yuzhakov et al. |
| 2004/0215224 | A1 | * | 10/2004 | Sakata et al. ................ 606/181 |
| 2005/0089861 | A1 | | 4/2005 | Allen |
| 2005/0177071 | A1 | | 8/2005 | Nakayama et al. |
| 2006/0036187 | A1 | | 2/2006 | Vos et al. |
| 2006/0129065 | A1 | | 6/2006 | Matsumoto et al. |
| 2006/0173379 | A1 | * | 8/2006 | Rasch-Menges et al. .... 600/583 |
| 2007/0060843 | A1 | * | 3/2007 | Alvarez-Icaza et al. ..... 600/583 |
| 2007/0118051 | A1 | * | 5/2007 | Korner et al. ............... 600/583 |

(Continued)

FOREIGN PATENT DOCUMENTS

DE 199 63 034 6/2001

(Continued)

*Primary Examiner*—Max Hindenburg
*Assistant Examiner*—Sean P Dougherty
(74) *Attorney, Agent, or Firm*—Bose McKinney & Evans LLP

(57) ABSTRACT

A puncturing device for generating a puncture wound to sample a body fluid is provided and comprises a press-on part or contact element to be pressed against a body part to generate a puncture, a test sensor for measuring a test parameter value, and an analytical unit for determining whether the value of the measured test parameter satisfies a predefined minimum requirement for successful sampling. In one embodiment, the value of the test parameter is monitored during a waiting period by the test sensor once the value satisfies the predefined minimum requirement. After the waiting period has elapsed, so long as the values of the test parameter monitored during the waiting period are in a range of values that predicts sampling to be successful, the analytical unit initiates a puncture.

27 Claims, 1 Drawing Sheet

U.S. PATENT DOCUMENTS

2007/0219463 A1* 9/2007 Briggs et al. ................ 600/583
2009/0275860 A1* 11/2009 Nakamura et al. .......... 600/573

FOREIGN PATENT DOCUMENTS

| DE | 103 32 283 | 2/2005 |
| EP | 1 360 933 | 11/2003 |
| EP | 1 535 572 | 6/2005 |
| EP | 1 570 783 | 9/2005 |
| EP | 1 598 011 | 11/2005 |
| EP | 1 611 848 | 1/2006 |

* cited by examiner

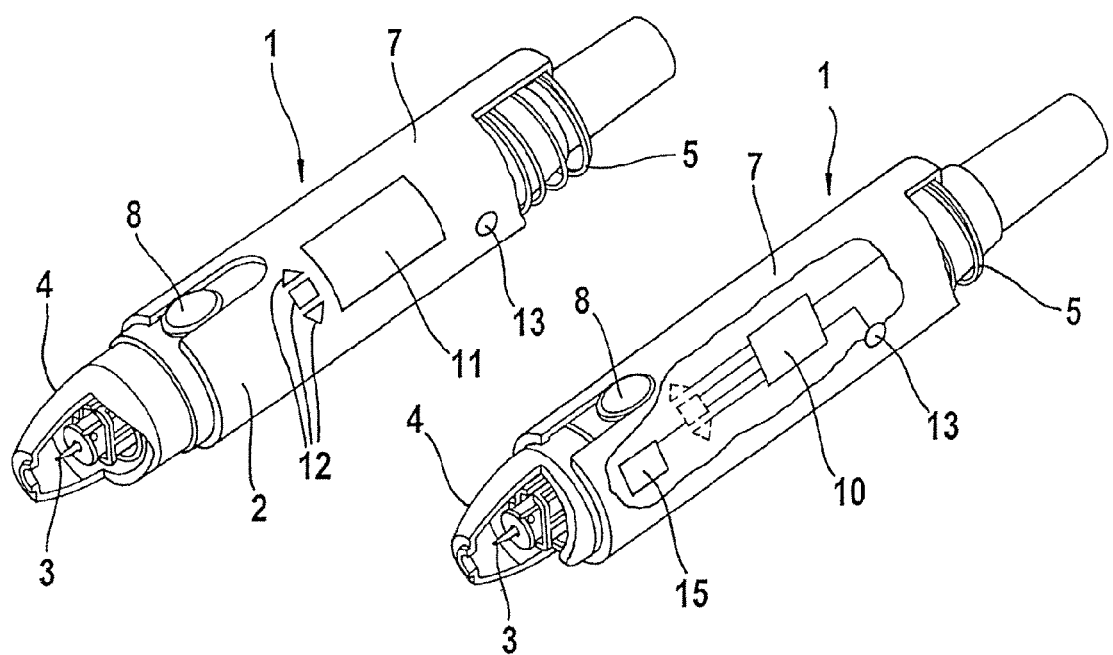

PUNCTURING DEVICE

RELATED APPLICATIONS

This application claims priority to European Patent Application No. 06 017 713.6, filed Aug. 25, 2006, which is hereby incorporated herein by reference.

BACKGROUND

Puncturing devices are used, for example, by diabetics who need to check their blood sugar level several times daily. Puncturing devices are usually used with disposable puncturing elements that are designed for single use. Puncturing elements of this type can be inserted into the puncturing device like a cartridge.

A persistent goal in the development of puncturing devices has been to generate puncture wounds with as little pain as possible and from which sufficient quantities of bodily fluid can be obtained. The depth of penetration is relevant to both the pain sensation and sampling size obtained. In general, the pain sensation and the quantity of bodily fluid obtained from the puncturing wound increase as the puncturing depth increases. Puncturing devices are therefore required to make the puncturing depth as small as possible to reduce the pain sensation, but also to make the puncture deep enough to produce a quantity of bodily fluid sufficient for measuring.

In order to reduce the risk of an unsuccessful puncture, puncturing devices having a pressure sensor are known, for example, in U.S. Pat. No. 5,879,311, in which a puncturing motion is initiated automatically as soon as a press-on part receives pressure in excess of a minimum pressure. A puncturing device having a built-in pressure sensor is also described in Publication No. EP 1 360 933. However, in this puncturing device, a puncture is not initiated automatically once a minimum pressure is reached, but rather the pressure exerted on a press-on part is displayed as falling within one of three general pressure ranges, viz., low, normal, and high. The puncturing motion is initiated by pressing a button on the device housing.

SUMMARY OF THE INVENTION

Embodiments incorporating the present invention address the disadvantages of the prior art and provide a puncturing device for generating puncture wounds that produce useful samples of bodily fluid and for measuring the bodily fluid samples. These embodiments advantageously produce puncture wounds that provide sufficient quantities of bodily fluid samples while maintaining convenience for the user and without increasing the pain felt by the user during a puncturing operation.

In an exemplary embodiment of the puncturing device, a press-on part or contact element is pressed against a body part at a sampling site where a puncture wound is generated. Additionally, the puncturing device includes a test sensor for measuring test parameters and an analytical unit connected to the test sensor for initiating a puncture and determining whether the test parameter value or condition satisfies a predefined minimum requirement. The minimum requirement is established for determining whether a particular puncturing operation will be successful. In the operating mode, the analytical unit initiates the puncture only after a waiting period has elapsed, wherein the waiting period starts as soon as the value of the test parameter or condition satisfies the minimum requirement. This test parameter or condition can be satisfied such that a puncture is always initiated after the waiting period has elapsed. In another embodiment, it may also be feasible to provide the user with the ability to prevent a puncture by actuating an operating element during the waiting period. In this embodiment, the non-actuation of the operating element becomes another necessary condition before the puncture can occur.

In one embodiment, the puncturing device advantageously has a signal unit connected to the analytical unit for indicating to a user whether the test parameter meets the predefined minimum requirement. This embodiment advantageously indicates the start of the waiting period to a user and the user can therefore adjust to and mentally prepare for the imminent puncture. In other puncturing devices known in the art, such as the device disclosed in U.S. Pat. No. 5,879,311, which automatically initiates a puncture immediately upon the attainment of a minimum exerted pressure, a user may be surprised by a puncture since no warning is given beforehand.

In another exemplary embodiment, once the value of a test parameter or condition reaches the predefined minimum requirement, the test sensor continuously monitors the parameter or condition during the waiting period. Once the waiting period has elapsed, the analytical unit initiates a puncture only if the test parameter value or condition remained within a predefined range of values during the waiting period that would indicate successful sampling is expected.

Although a puncture is initiated automatically, this occurs only after a predefined waiting period has elapsed. This advantageously allows a user to prevent a puncture even after pressing the press-on part or contact element of the puncturing device against a body part, for example, in order to reposition the device and take a sample at a different sampling site.

The option of discontinuing a puncturing operation is otherwise provided only by devices in which a user needs to actuate an initiation element in order to initiate the puncture. However, requiring users to actuate the initiation element is inconvenient to many users and may induce mental stress or anxiety to some users. In contrast to other puncturing devices, an exemplary embodiment of a puncturing device incorporating the present invention advantageously provides the combined automatic initiation and user control over the puncturing process.

In another embodiment of the puncturing device, the test sensor is a pressure sensor that can be used to determine whether the exerted pressure exceeds a predefined minimum value. Also, the temperature of the body part at the sampling site or the blood supply status can be measured and analyzed as test parameters or conditions.

It is also feasible to select a minimum requirement that defines the beginning of the waiting period once it is reached, and then deviate from the minimum requirement during the waiting period. For example, in one embodiment the minimum requirement can be set at minimum pressure p1, and the predefined range of values can comprise all pressures above a pressure value p2, in which the value of the pressure p2 is lower than minimum pressure p1. In this example, the waiting period can be prevented so long as the pressure p2 is selected such that successful sampling can occur at pressure p2. The use of mechanical sensors, such as a snap disc, is often associated with hysteresis such that a minimum pressure p1 required to switch the snap disc is automatically higher than a pressure p2, below which the snap disc switches back to its original configuration.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIG. 1 is a perspective view of a puncturing system with a puncturing device; and FIG. 2 is a perspective view of the puncturing system of FIG. 1 with a portion of the puncturing device being removed to illustrate an analytical unit.

Corresponding reference numerals are used to indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

As shown in FIG. 1, a puncturing device 2 and lancets 3 (that are intended for single use and are inserted into the puncturing device 2) jointly form a puncturing system 1. In order to generate a puncturing wound, a press-on part or contact element 4 of the puncturing device 2 is pressed against a body part of a user. In the process, the press-on part or contact element 4 shifts or moves with respect to the device housing 7. If the pressure exerted on the contact element 4 exceeds a minimum pressure that is measured against the force of a spring 5, a switch (not shown) is closed. The closing of the switch is an indication that successful sampling will likely occur.

In the exemplary embodiment shown in FIG. 1, the spring 5 forms part of a test sensor, and the exerted pressure and/or the information concerning whether the exerted pressure exceeds the predefined minimum pressure is used as a test parameter that depends on the location of the sampling site and/or the position of the press-on part or contact element 4 with respect to the sampling site. However, instead of a pressure sensor, other test sensors may also be used, e.g., for measuring the temperature or the blood supply status.

The puncturing device further comprises an analytical unit that is shown in FIG. 2. The analytical unit determines whether the value of the measured test parameter meets a predefined minimum requirement that is needed to achieve successful sampling. For example, in the exemplary embodiment shown in FIG. 2, this minimum requirement is the force required to compress the spring 5.

The puncturing device 2 operates in an operating mode and the value of the test parameter, once it exceeds the predefined minimum requirement, is monitored by the test sensor 5 during a waiting period. After the waiting period elapses, if all test parameter values measured during the waiting period fall within the predefined range of values that will likely produce a successful sampling, the analytical unit 10 initiates a puncture. The range of values consists of the test parameter values that satisfy the predefined minimum requirement. Accordingly, a puncture occurs if the test parameter value satisfies the predefined minimum requirement during the entire waiting period, such that the value never falls below the minimum exerted pressure that is defined by the force of the spring 5.

The analytical unit 10 can, for example, be an ASIC (Application Specific Integrated Circuit) or a microprocessor. In the puncturing device 2 shown in FIG. 2, the analytical unit 10 automatically initiates a puncture as soon as the minimum exerted pressure predefined by the spring force of the spring 5 is exceeded for a period of at least 0.5 sec, and preferably at least 0.8 sec, such that the switch (not shown) remains closed due to the shift or movement of the press-on part or contact element 4. Opening the switch causes the waiting period to restart. The elapsing of the waiting period can be detected by a RC component or a clock in the form of a clocked counter.

Additionally, the waiting period can be set by a user. For this purpose, the puncturing device 2 comprises a display facility or element 11 in the form of a liquid crystal display, such as a segment display, and an operating facility with manually actuated operating elements 12. In addition, the operating elements 12 can set the minimum requirement, such as the minimum pressure required for the initiation of a puncture, in order to conform the puncturing device 2 to the individual needs of a user.

As soon as the value of the measured test parameter satisfies the predefined minimum requirement, this is indicated to a user by a signaling unit 13 that is attached to the analytical unit 10. The signaling unit 13 can be an optical signaling unit that generates a light signal to indicate that the test parameter meets the predefined minimum requirement. However, an acoustic signaling unit or a signaling unit that vibrates can be used as well.

It is advantageous to also use the signaling unit 13 during the waiting period to indicate to the user the progression of time. Accordingly, the signaling unit 13 generates a signal during the waiting period that indicates the amount of time that has already elapsed. For example, the brightness of the signal generated could change with the progression of time. Therefore, a user can recognize how much time remains until the automatic initiation of a puncture. Another option is for the signaling unit 13 to generate a flashing signal whose frequency changes during the waiting period by becoming faster. An acoustic signaling unit or a signaling unit that generates a vibratory signal can be used to display the progression of time during the waiting time interval by changing the signal intensity or its frequency. Advantageously, the display facility or element 11 can be used as the signaling unit to indicate to a user whether the test parameter meets the predefined minimum requirements and how much of the waiting period has elapsed at the time the signal is generated. For example, a series of bars can be shown on the display facility or element 11 and the number of bars being displayed changes during the waiting period such that a puncture is initiated as soon as the last bar disappears. Another possible display is an image of an hourglass running empty during the waiting period.

The operating elements 12 can also be used to switch the puncturing device 2 to a different operating mode in which a puncture is triggered by an initiation element 8 and is actuated by a user as soon as the value of the test parameter meets the predefined minimum requirement. The initiation element 8 shown in FIGS. 1-2 is a button. However, it is also possible to provide the initiation element 8 in such a way that, for example, actuation is caused by an increase in the pressure applied by the press-on part or contact element 4 against a body part or having to shift or move the press-on part or contact element 4 with respect to the device housing 7 an additional distance.

It is particularly favorable to lock the initiation element 8 in this operating mode by providing a securing facility (not shown) until the value of the test parameter meets the predefined minimum requirement. Accordingly, a user can generate a puncture only when successful sampling is expected. A securing facility of this type can be, for example, integrated into the analytical unit 10.

User convenience is further enhanced in puncturing devices 2 that are used not only to generate a puncture wound, but which also comprise a measuring facility or unit 15 for testing a body fluid sample. Common portable analytical devices used for determining the blood glucose content contain suitable measuring facilities or units 15 such as for photometric or electrochemical testing. For example, an exemplary reception unit and test field for electrochemical or photometric measurements of an analyte concentration can be integrated in the puncturing element or lancet 3. Puncturing elements that comprise a capillary channel, into which body fluid is transported during a collection phase to a test field, are known in the prior art, for example, in U.S. Publication No. 20030171699, which is hereby incorporated by reference. In puncturing devices of this type, collection of the bodily fluid sample does not require additional handling steps for a user. This is an important advantage, in particular, for users whose dexterity is restricted by age or disease.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A puncturing device for generating a puncture in a body part for sampling a body fluid, comprising:
    a housing having a contact element adapted to be pressed against a body part;
    a sensor for detecting a test parameter;
    an analytical unit disposed in the housing and in communication with the sensor, the analytical unit determining whether the detected test parameter meets a test condition and initiating a waiting period that begins when the test parameter meets the test condition, the analytical unit determining whether to trigger the puncturing operation at the end of the waiting period; and
    a signaling unit that generates a user-recognizable optical, acoustic or vibratory signal indicating elapsed time of the waiting period;
    wherein the sensor monitors the test parameter during the waiting period and the analytical unit determines whether the test parameter falls within a predefined range during the waiting period, further wherein the analytical unit initiates the puncturing operation at the end of the waiting period if the test parameter falls within the predefined range during the waiting period.

2. The puncturing device of claim 1, further comprising a spring that compresses when the contact element presses against the body part, wherein the contact element moves relative to the housing.

3. The puncturing device of claim 2, wherein the sensor comprises a pressure sensor that detects pressure exerted on the contact element.

4. The puncturing device of claim 1, wherein the waiting period is at least 0.5 seconds.

5. The puncturing device of claim 1, further comprising an operating element that allows a user to adjust the waiting period.

6. The puncturing device of claim 5, wherein the operating element is configured to allow a user to set the test condition.

7. The puncturing device of claim 1, further comprising a signaling unit indicates whether the test parameter meets the test condition.

8. The puncturing device of claim 1, further comprising a measuring unit disposed in the housing and configured to test a body fluid sample.

9. The puncturing device of claim 1, further comprising a manually actuated element to trigger a puncture.

10. The puncturing device of claim 1, wherein the test sensor comprises a pressure sensor and the test parameter comprises pressure exerted on the contact element, further wherein the analytical unit initiates the puncturing operation at the end of the waiting period if the pressure exerted on the contact element remains within a predefined range of values during the waiting period.

11. A puncturing device for generating a puncture in a body part for sampling a body fluid, comprising:
    a housing having a contact element adapted to be pressed against a body part;
    a sensor for detecting a test parameter;
    an analytical unit disposed in the housing and in communication with the sensor, the analytical unit determining whether the detected test parameter meets a test condition and initiating a waiting period that begins when the test parameter meets the test condition, the analytical unit determining whether to trigger a puncturing operation at the end of the waiting period; and
    a signaling unit that generates a first signal indicating whether the test parameter meets the test condition and generates a second signal indicating the start of the waiting period, the first and second signals comprising user-recognizable optical, acoustic or vibratory signals.

12. The puncturing device of claim 11, wherein the sensor monitors the test parameter during the waiting period and the analytical unit determines whether the test parameter falls within a predefined range during the waiting period, further wherein the analytical unit initiates the puncturing operation at the end of the waiting period if the test parameter falls within the predefined range during the waiting period.

13. The puncturing device of claim 11, further comprising:
    a spring that compresses when the contact element presses against the body part, wherein the contact element moves relative to the housing; and
    a pressure sensor that detects pressure exerted on the contact element, wherein the test parameter comprises pressure exerted on the contact element.

14. The puncturing device of claim 11, further comprising an operating element that allows a user to adjust the waiting period.

15. The puncturing device of claim 11, wherein the signaling unit generates a third user-recognizable optical, acoustic or vibratory signal indicating time remaining in the waiting period.

16. The puncturing device of claim 11, wherein the sensor comprises a pressure sensor and the test parameter comprises pressure exerted on the contact element, further wherein the analytical unit initiates the puncturing operation at the end of the waiting period if the pressure exerted on the contact element remains with a predefined range of values during the waiting period.

17. A puncturing device for generating a puncture in a body part for sampling a body fluid, comprising:

a housing having a contact element adapted to be pressed against a body part;

a sensor for detecting a test parameter;

an analytical unit disposed in the housing and in communication with the sensor, the analytical unit determining whether the detected test parameter meets a test condition and initiating a waiting period that begins when the test parameter meets the test condition, the analytical unit determining whether to trigger a puncturing operation at the end of the waiting period; and a signaling unit that generates a first signal indicating whether the test parameter meets the test condition and generates a second signal indicating elapsed time of the waiting period, the first and second signals comprising user-recognizable optical, acoustic or vibratory signals.

18. The puncturing device of claim 17, wherein the sensor monitors the test parameter during the waiting period and the analytical unit determines whether the test parameter falls within a predefined range during the waiting period, further wherein the analytical unit initiates the puncturing operation at the end of the waiting period if the test parameter falls within the predefined range during the waiting period.

19. The puncturing device of claim 17, further comprising:

a spring that compresses when the contact element presses against the body part, wherein the contact element moves relative to the housing; and a pressure sensor that detects pressure exerted on the contact element, wherein the test parameter comprises pressure exerted on the contact element.

20. The puncturing device of claim 17, further comprising an operating element that allows a user to adjust the waiting period.

21. The puncturing device of claim 17, wherein the signaling unit generates a third user-recognizable optical, acoustic or vibratory signal indicating the start of the waiting period.

22. The puncturing device of claim 17, wherein at least one of the first and second signals comprises an optical signal.

23. The puncturing device of claim 22, further comprising a display that displays the optical signal.

24. The puncturing device of claim 11, wherein at least one of the first and second signals comprises an optical signal.

25. The puncturing device of claim 24, further comprising a display that displays the optical signal.

26. The puncturing device of claim 1, wherein the signaling unit generates an optical signal indicating whether the test parameter meets the test condition.

27. The puncturing device of claim 26, further comprising a display that displays the optical signal.

* * * * *

UNITED STATES PATENT AND TRADEMARK OFFICE
CERTIFICATE OF CORRECTION

| | | |
|---|---|---|
| PATENT NO. | : 7,766,847 B2 | Page 1 of 1 |
| APPLICATION NO. | : 11/845051 | |
| DATED | : August 3, 2010 | |
| INVENTOR(S) | : Uwe Kraemer et al. | |

It is certified that error appears in the above-identified patent and that said Letters Patent is hereby corrected as shown below:

In col. 6, line 6, please remove the words [further comprising a] and replace with --wherein the--

In col. 6, line 14, please remove the word [test]

Signed and Sealed this

Twenty-eighth Day of September, 2010

David J. Kappos
*Director of the United States Patent and Trademark Office*